(12) United States Patent
Benn et al.

(10) Patent No.: US 10,111,816 B2
(45) Date of Patent: Oct. 30, 2018

(54) COMPOSITION FOR ALTERING THE COLOR OF KERATIN FIBERS

(71) Applicant: L'OREAL, Paris (FR)

(72) Inventors: Mark Benn, Union, NJ (US); Michael Degeorge, Old Bridge, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/819,350

(22) Filed: Aug. 5, 2015

(65) Prior Publication Data

US 2017/0035667 A1 Feb. 9, 2017

(51) Int. Cl.
| | |
|---|---|
| *A61Q 5/10* | (2006.01) |
| *A61K 8/41* | (2006.01) |
| *A61K 8/25* | (2006.01) |
| *A61K 8/20* | (2006.01) |
| *A61K 8/19* | (2006.01) |
| *A61K 8/22* | (2006.01) |
| *A61K 8/34* | (2006.01) |
| *A61K 8/49* | (2006.01) |

(52) U.S. Cl.
CPC .................. *A61K 8/41* (2013.01); *A61K 8/19* (2013.01); *A61K 8/20* (2013.01); *A61K 8/22* (2013.01); *A61K 8/25* (2013.01); *A61K 8/347* (2013.01); *A61K 8/411* (2013.01); *A61K 8/415* (2013.01); *A61K 8/492* (2013.01); *A61K 8/494* (2013.01); *A61K 8/4926* (2013.01); *A61Q 5/10* (2013.01); *A61K 2800/4324* (2013.01); *A61K 2800/88* (2013.01)

(58) Field of Classification Search
CPC ... A61K 8/41; A61K 8/25; A61K 8/19; A61K 8/22; A61K 2800/88; A61K 2800/4324; A61Q 5/10
USPC .......................................................... 8/405
See application file for complete search history.

(56) References Cited

U.S. PATENT DOCUMENTS

| | | | |
|---|---|---|---|
| 3,915,921 A | 10/1975 | Schlatzer, Jr. | |
| 4,003,699 A | 1/1977 | Rose et al. | |
| RE30,199 E | 1/1980 | Rose et al. | |
| 4,509,949 A | 4/1985 | Huang et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,766,576 A | 6/1998 | Lowe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |
| 2008/0087293 A1* | 4/2008 | Glenn ................ A45D 19/0008 132/210 |
| 2010/0263138 A1* | 10/2010 | Audousser ............... A61K 8/25 8/407 |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0080976 A1 | 6/1983 |
| EP | 0714954 A2 | 6/1996 |
| EP | 0770375 A1 | 5/1997 |
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |

OTHER PUBLICATIONS

Todd, Charles, et al., "Volatile Silicone Fluids for Cosmetic Formulations," Cosmetics and Toiletries, vol. 91, Jan. 1976, pp. 29-32.
International Preliminary Report on Patentability for Application No. PCT/US2016/045870, dated Feb. 15, 2018.

* cited by examiner

*Primary Examiner* — Eisa B Elhilo
(74) *Attorney, Agent, or Firm* — The Marbury Law Group, PLLC

(57) ABSTRACT

Disclosed are hair color bases, hair color compositions, and methods for altering the color of hair. Hair color bases comprise a buffer system including ammonium chloride, sodium metasilicate, ammonium hydroxide, and monoethanolamine (MEA). Hair color compositions comprise a hair base comprising a buffer system including ammonium chloride, sodium metasilicate, ammonium hydroxide, and monoethanolamine (MEA), and an oxidizing component.

15 Claims, No Drawings

COMPOSITION FOR ALTERING THE COLOR OF KERATIN FIBERS

TECHNICAL FIELD

The present disclosure relates to a hair color base that comprises a buffer system, hair color compositions comprising a hair color base comprising a buffer system and an oxidizing component, and methods of altering the color of keratinous fibers.

BACKGROUND

Consumers desire to use cosmetic and personal care compositions that enhance the appearance of keratin fibers, such as hair, by changing the color of the hair and/or by imparting various properties to hair, for example, shine and conditioning. The process of changing the color of hair can involve depositing an artificial color onto the hair, which provides a different shade or color to the hair, and/or lifting the color of the hair.

The process of lifting the color of hair, also known as lightening, generally requires the use of compositions that comprise at least one oxidizing agent to lighten the color of dark hair to lighter shades. When colorants or dye compounds such as oxidation dye precursors and direct dyes are present in these compositions, such compositions can change or deposit color and lighten the color of hair at the same time. Conventional hair coloring products are permanent dye compositions comprising oxidation dye precursors, which are also known as primary intermediates or couplers. These oxidation dye precursors are colorless or weakly colored compounds which, when combined with oxidizing agents, give rise to colored complexes by a process of oxidative condensation.

Lightening or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions may require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While such hair dyeing and/or color lifting compositions can effectively alter the color of hair, these compositions can damage the hair fibers and/or irritate the scalp due to having excessively high levels of alkalinity.

Thus, in order to reduce or avoid the drawbacks above, as well as to improve the cosmetic performance of hair color lifting and hair dyeing compositions, the use of new and additional ingredients and novel combinations of ingredients are continuously sought. However, the choice of ingredients or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It is therefore, desirable to provide the consumer with compositions and methods that can lift the color of hair and additionally, deposit color onto hair in an efficient or improved manner, while preventing excess damage to the hair and/or providing other cosmetic advantages such as shine, conditioning, and a healthy appearance to the hair.

Thus, an objective of the present disclosure is to provide novel compositions for altering the color of hair by lifting or lightening the color of the hair and optionally depositing color, while minimizing the damage to the hair and other adverse effects to the consumer.

BRIEF SUMMARY

The disclosure relates to compositions and methods for changing or altering the color of hair. In various embodiments, the compositions and methods described allow one to achieve a desired level of color lift in tone. In further embodiments, the compositions and methods allow one to additionally deposit color onto hair. Such advantages are provided according to various embodiments with minimal to no damage to the hair.

In order to achieve these and other advantages, the disclosure relates to a hair color base comprising a buffer system, wherein the buffer system comprises ammonium chloride, sodium metasilicate, ammonium hydroxide, and monoethanolamine (MEA). The hair color base may optionally comprise at least one colorant component. In further embodiments, the disclosure relates to a hair color composition comprising: a hair color base comprising a buffer system, an oxidizing component, and optionally one or more colorant compounds.

In yet further embodiments, the disclosure relates to methods of coloring, lightening, and/or lifting the tone of the hair using a hair color base comprising a buffer system according to the disclosure. For example, methods may comprise contacting the hair with a composition for lifting the color of hair for a sufficient period of time to achieve a desired level of lift of the color of the hair, wherein the composition is formed from mixing a hair color base comprising a buffer system with an oxidizing component, wherein the buffer system comprises ammonium chloride, sodium metasilicate, ammonium hydroxide, and monoethanolamine (MEA); and the pH of the composition for altering the color of hair ranges from about 8.5 to about 10.

In still further embodiments, the disclosure relates to a multi-compartment kit for altering the color of the hair, comprising (a) a first compartment comprising a hair color base comprising a buffer system, wherein the buffer system comprises ammonium chloride, sodium metasilicate, ammonium hydroxide, monoethanolamine (MEA), wherein the hair color base optionally comprises a colorant compound; and (b) a second compartment comprising an oxidizing composition comprising at least one oxidizing agent.

DETAILED DESCRIPTION

It has been surprisingly and unexpectedly discovered that when the hair color base of the present disclosure contains an oxidizing agent or when it is mixed with an oxidizing agent or a composition containing an oxidizing agent, improved hair color lightening or lifting effects are achieved, while minimizing damage to the hair. For example, the composition provides good uniformity of lift along the fiber between the tip and the root of the hair (also called the selectivity of lightening).

Altering or lifting the color of hair can be achieved with minimal damage to the hair using the process and compositions of the present disclosure, and particularly, using a hair color base chosen to have a pH of from about 8.5 to about 10, comprising a buffer system as described herein. Moreover, it was surprisingly and unexpectedly discovered that by using the compositions of the present disclosure, it was possible to achieve acceptable lift to the color of the hair that corresponds to an increase in tone height in an amount ranging from 0.5 to 4, such as from about 1 to about 3, or from about 1.5 to about 2.5, while minimizing damage to the hair.

Furthermore, when the hair color composition of the present disclosure additionally contains colorant/dye compounds, it was surprisingly and unexpectedly discovered that the composition can also deposit color effectively and comparably to, if not better than, traditional permanent alkaline commercial hair dyes, while maintaining a lower pH, and thus, the compositions and processes of the present disclosure can provide for improved color visibility and better color coverage, with less damage to the hair.

The hair color base compositions may be mixed with an oxidizing agent or composition containing at least one oxidizing agent. The resulting composition comprising the hair color base and the oxidizing composition is used for lifting or lightening the composition of the hair as described herein. When the hair color composition or hair color base additionally contains a colorant compound, the resulting composition is also used for depositing color onto hair.

The hair color base and/or compositions for altering the color of hair may be employed to lift or lighten the color of hair. According to various embodiments, a process for lifting or altering the color of keratin fibers, such as hair, is provided, comprising applying to the hair a hair color base composition, an oxidizing component, and optionally at least one colorant.

Hair Color Base

The hair color base compositions according to the disclosure comprise a buffer system. The components of the buffer system of the hair color base may be chosen to maintain an alkaline pH of the compositions, before and/or after the hair hair color base is mixed with the oxidizing component and/or colorant compound(s). Thus, according to one embodiment, the pH of the hair color base ranges from about 8.5 to about 10.

The buffer system comprises ammonium chloride, sodium metasilicate, ammonium hydroxide, and monoethanolamin5e ("MEA"). The ammonium chloride, ammonium hydroxide, and MEA may operate to maintain the alkaline pH, may provide lift to hair, and may facilitate the incorporation of colorant compounds into hair. Unexpectedly, it was determined that the combination increased lift, without affecting pH.

It is understood that the hair color base and/or buffer system may comprise additional components, but such components should be chosen with care to maintain a pH of the hair color base and/or the degree of lift imparted within an acceptable variation.

The following weight percentages are based on the total weight of the hair color base. The buffer system may include from about 3 to about 12 wt % ammonium chloride, such as about 5 to about 10 wt %, about 6 to about 8 wt %, or about 6.5 to about 7.5 wt %. The buffer system may include from about 1 to about 5 wt % sodium metasilicate, such as about 3 to about 4 wt %, about 2 to about 4 wt %, or about 2.5 to about 3.5 wt %. The buffer system may include from about 1 to about 5 wt % ammonium hydroxide, such as about 3 to about 4 wt %, about 2 to about 4 wt %, or about 2.5 to about 3.5 wt %. The buffer system may include from about 1 to about 5 wt % MEA, such as about 2 to about 4 wt %, about 2.5 to about 4.5 wt %, or about 3 to about 4 wt %.

For example, according to one exemplary and non-limiting embodiment, the buffer system may include about 7.0 wt % ammonium chloride, about 3.0 wt % sodium metasilicate, about 3.0 wt % ammonium hydroxide, and about 3.5 wt % MEA, based on the total weight of the hair color base.

Hair Color Compositions

Hair color compositions according to the disclosure comprise the hair color base, at least oxidizing component, optionally at least one colorant compound, and optionally at least one other component suitable for use in cosmetic compositions, and in particular in hair coloring or lightening compositions.

It is understood that the oxidizing component, colorant component, and any optional components may be present in the hair color base composition itself, or may be present in a separate composition that is mixed with the hair color base before application to the hair, and that any reference to a component being present in the hair color base is intended to also include disclosure of the component in a separate composition that is mixed with the hair color base before application to the hair, and that any reference to a component being present in the hair color composition includes disclosure of the component in the hair color base composition.

Oxidizing Component

The hair color composition according to the disclosure comprises at least one oxidizing component. The oxidizing component may be an oxidizing agent, or may be a composition comprising an oxidizing agent ("oxidizing composition"), which terms are used interchangeably herein without intending to be limiting. In various embodiments, the oxidizing component may be provided as a separate component from the hair color base, and be mixed with the hair color base, for example at a time just before use, such as about 1 to about 20 minutes before application to the hair.

The oxidizing agent may be, for example, chosen from peroxides, persulfates, perborates, percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be an oxidizing component.

In one embodiment, the oxidizing agent is hydrogen peroxide present in an aqueous solution whose titre may range from 1 to 40 volumes, such as from 5 to 40 volumes or such as from 5 to 20 volumes.

In another embodiment, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof. In certain embodiments, the oxidizing agent is hydrogen peroxide.

In general, the oxidizing agent will be present in an amount of from about 0.05 to about 50% by weight, such as from about 0.1% to about 30% by weight, or such as from about 0.1% to about 20% by weight, or such as from about 1% to about 10% by weight, based on the total weight of the oxidizing composition.

In one embodiment, the oxidizing composition is aqueous or is in the form of an emulsion. In another embodiment, the oxidizing composition is substantially anhydrous.

The term "substantially anhydrous" means that the oxidizing composition is either completely free of water or contains no appreciable amount of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, for example water, organic solvents, or mixtures thereof.

When the oxidizing composition is substantially anhydrous, the oxidizing composition may comprise at least one solvent chosen from organic solvents. Suitable organic solvents for use in the oxidizing composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The organic solvents for use according to the present disclosure can be volatile or non-volatile compounds. The organic solvent may, for example, be present in an amount ranging from about 0.5% to about 70% by weight, such as from about 2% to about 60% by weight, such as from about 5 to about 50% by weight, relative to the total weight of the oxidizing composition.

The oxidizing composition may be in the form of a powder, gel, liquid, foam, lotion, cream, mousse, and emulsion.

Colorant

The hair color base and/or hair color composition according to the disclosure may optionally comprise at least one colorant compound. In various embodiments, one or more colorants may be present in the hair color base composition, in a further embodiment one or more colorants may be present in a separate composition that is mixed with the hair color base before use, and in yet a further embodiment one or more colorants may be present in the hair color base and one or more colorants may be present in a separate composition that is mixed with the hair color base before use.

In various embodiments, the at least one colorant chosen from oxidative dye precursors, direct dyes, pigments, and mixtures thereof.

The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols, meta-aminophenols, and heterocyclic bases, and the addition salts thereof.

Among the para-phenylenediamines that may be mentioned, for example, are para-phenylenediamine, para-toluenediamine (toluene-2,5-diamine), 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, hydroxypropyl bis(n-hydroxyethyl-p-phenylenediamine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be chosen.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the meta-aminophenols, 3-aminophenol and salts thereof, may be mentioned.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1

026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-α-hydroxyethoxy-3-amino-pyrazolo[1,5-a]pyridine; 2-(4-dimethylpyperazinium-1-yl)-3-amino-pyrazolo[1,5-a]pyridine; hydroxyethoxy aminopryazolopyridine, and the addition salts thereof.

More particularly oxidation bases that are useful in the present disclosure are selected from 3-aminopyrazolo-[1,5-a]-pyridines and optionally substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more ($C_1$-$C_6$)alkyl, such as di($C_1$-$C_4$)alkylpiperazinium; or
(c) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used. According to some embodiments, 2,3-diaminodihydropyrazolo pyrazolone dimethosulfonate may also be used. Optionally, a 4,5-diaminopyrazole may be used, for example 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one. For example, 2,3-Diamino-6,7-dihydro-1H,5H-pyrazolo[1,2-a]pyrazol-1-one and/or a salt thereof may be used.

According to some embodiments, 2,3-diaminodihydropyrazolo pyrazolone dimethosulfonate may be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof may be used as heterocyclic bases.

Compositions according to the invention may optionally comprise one or more couplers advantageously chosen from those conventionally used in the dyeing or coloring of keratin fibers. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)-benzene (2,4 diaminophenoxyethanol HCL), 2-amino-4-(β-hydroxyethylamino)-1-methoxybenzene (2-methyl-5-hydroxyethylaminophenol), 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethyl-amino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 4-amino-2-hydroxytoluene, 2-methylresorcinol, 4-chlororesorcinol, and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may, for example, represent from 0.001% to 10% by weight relative to the total weight of the composition, such as from 0.005% to 5% by weight relative to the total weight of the compositions of the present disclosure.

The coupler(s), if they are present, each advantageously represent from 0.001% to 10% by weight relative to the total weight of the composition, such as from 0.005% to 5% by weight relative to the total weight of the compositions of the present disclosure.

Compositions according to the invention may optionally comprise b) one or more synthetic or natural direct dyes, chosen from anionic and nonionic species, e.g. cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

In various embodiments, direct dyes are cationic direct dyes. Mention may be made of the hydrazono cationic dyes of formulas (Va) and (V'a), the azo cationic dyes (VIa) and (VI'a) and the diazo cationic dyes (VIIa) below:

  (Va)

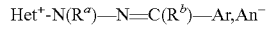  (V'a)

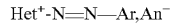  (VIa)

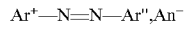  (VI'a) and

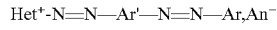  (VIIa)

in which formulas (Va), (V'a), (VIa), (VI'a) and (VIIa):

Het$^+$ represents a cationic heteroaryl radical, optionally bearing an endocyclic cationic charge, such as imidazolium, indolium or pyridinium, optionally substituted preferentially with one or more $(C_1-C_8)$ alkyl groups such as methyl;

Ar$^+$ representing an aryl radical, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy;

Ar'' is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

R$^a$ and R$^b$, which may be identical or different, represent a hydrogen atom or a group $(C_1-C_8)$alkyl, which is optionally substituted, preferentially with a hydroxyl group;

or alternatively the substituent R$^a$ with a substituent of Het$^+$ and/or R$^b$ with a substituent of Ar and/or R$^a$ with R$^b$ form, together with the atoms that bear them, a (hetero)cycloalkyl;

particularly, R$^a$ and R$^b$ represent a hydrogen atom or a group $(C_1-C_4)$alkyl, which is optionally substituted with a hydroxyl group;

An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954

In various embodiments, the cationic part is derived from the following derivatives:

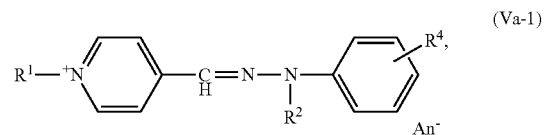

(Va-1)

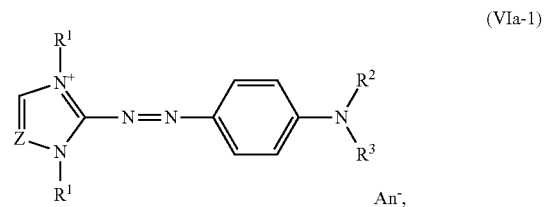

(VIa-1)

formulae (V-1) and (VI-1) with:

R$^1$ representing a $(C_1-C_4)$ alkyl group such as methyl;

R$^2$ and R$^3$, which are identical or different, represent a hydrogen atom or a $(C_1-C_4)$alkyl group, such as methyl; and R$^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, R$^4$ is a hydrogen atom, Z represents a CH group or a nitrogen atom, preferentially CH;

An$^-$ represents an anionic counter-ion such as mesylate or halide.

In various embodiments, the dye of formulae (Va-1) and (VIa-1) is chosen from Basic Red 51, Basic Yellow 87 and Basic Orange 31 or derivatives thereof:

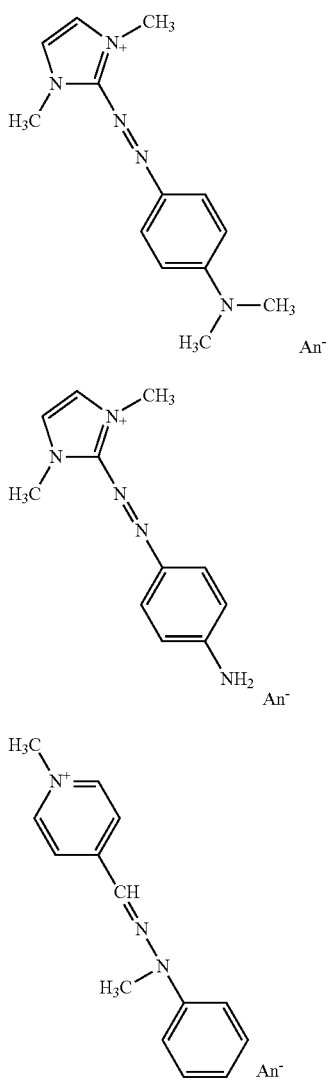

Basic Red 51

Basic Orange 31

Basic Yellow 87

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used. When present, the direct dye(s) may, for example, be present in an amount ranging from 0.001% to 10% by weight, such as from 0.005% to 5% by weight of the total weight of the hair color base or hair color composition in which they are present.

Optional Components

The hair color base and/or hair color composition according to the disclosure can comprise any auxiliary or additional component suitable for use in cosmetic compositions, and in particular suitable for hair coloring or lightening compositions. Such components may include, but are not limited to, cosmetically acceptable solvents, silicone compounds, thickening agents, rheology modifying agents such as acrylic polymers, anionic, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances, emulsifying agents other than fatty substances, fillers, structuring agents, propellants, shine agents, conditioning agents, antioxidants or reducing agents, penetrants, sequestrants, fragrances, buffers, dispersants, conditioning agents, for instance volatile or non-volatile, modified or unmodified silicones, ceramides, preserving agents, opacifiers, sunscreen agents, and antistatic agents. Acids, for example citric acid, can affect the pH of the system resulting in loss of lift. As such, optional auxiliary or additional components will be chosen so as to minimize any detrimental effect to the advantages of the hair color bases and compositions described herein.

According to some embodiments the antistatic agent may include a hexadimethrine chloride polymer. In various embodiments, the sequestering agents may include ethylenediaminetetraacetic acid (EDTA) or its conjugate base. The hair color base and oxidizing compositions of the present disclosure according to the disclosure can be in various forms, such as in the form of liquids, creams, liquid-gels, liquid-creams, gels, lotions or pastes.

Typically, the foregoing optional components may be present in amounts up to about 25%, such as about 1% to about 20%, or about 2% to about 10%, by weight of the composition, when present, although different amounts are also contemplated.

The hair color base and/or hair color composition according to the disclosure can comprise a cosmetically acceptable solvent, for example as a dye support when a hair dye composition is contemplated. The cosmetically acceptable solvent can comprise water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin. The organic solvents for use according to the present disclosure can be volatile or non-volatile compounds.

When present, the organic solvent may be employed according to the present disclosure in an amount ranging from about 0.1% to about 25% by weight, such as from about 1% to about 15% by weight, or such as from about 2% to about 8% by weight, or such as from about 3% to about 7% by weight, or such as about 4% to 6% by weight, based on the total weight of the hair color base and/or hair color composition in which it is present. For example, the hair color base may include 0.6 wt % of a carbomer (4% solution).

In various exemplary embodiments, the cosmetically acceptable solvent may be employed according to the present disclosure in an amount ranging from about 1% to about 60% by weight, or such as from about 5% to about 30% by weight, such as from about 5% to about 25% by weight, or such as from about 5% to about 20% by weight, based on the total weight of the hair color base.

The hair color base and/or hair color composition according to the disclosure can also further comprise at least one nonionic surfactant. In general, nonionic surfactants having a Hydrophilic-Lipophilic Balance (HLB) of from 8 to 20, may be used in the present disclosure. Including at least one nonionic surfactant may help stabilize the hair color base and/or hair color composition when oxidative dye precursors are present in the composition. Thus, in certain embodiments, when colorant compounds such as oxidative dye precursors are present, at least one nonionic surfactant may also be present.

By way of example only, nonionic surfactants useful in the compositions of the present disclosure may be chosen from those disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, for example in the $C_{16}$-$C_{40}$ range, or in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being useful examples. The alkyl chain may be linear, branched, saturated, or unsaturated. Of these alkoxylated non-ionic surfactants, the alkoxylated alcohols may be chosen, such as ethoxylated alcohols and propoxylated alcohols. The alkoxylated alcohols may be used alone or in mixtures thereof. The alkoxylated alcohols may also be used in mixtures with those alkoxylated materials disclosed hereinabove.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-20 (a stearyl alcohol ethoxylate having an average degree of ethoxylation of 20), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Croda, Inc., Edison, N.J. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600 CS and 625 CS), all the above-identified polyglucosides APG® are available from BASF Corp. Also useful herein are sucrose ester surfactants such as sucrose cocoate and sucrose laurate.

Other nonionic surfactants suitable for use according to the present disclosure are glyceryl esters and polyglyceryl esters, including but not limited to, glyceryl monoesters, such as glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters, e.g. sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate may be used as emulsifiers.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, such as ethoxylated or propoxylated derivatives of these materials. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20). According to some embodiments TWEEN®-21 (polyoxyethylene (4) sorbitan monolaurate) may be used.

Nonionic surfactants may be those formed from a fatty alcohol, a fatty acid, or a glyceride with a $C_4$ to $C_{36}$ carbon chain, such as a $C_{12}$ to $C_{18}$ carbon chain, or a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is optionally greater than or equal to 8. In various embodiments, the nonionic surfactants contain ethoxylate in a molar content of from 10-25, such as from 10-20 moles.

When present, the nonionic surfactant will typically be present in the hair color composition in an amount of from about 0.1% to about 30% by weight, such as from about 0.5% to 20% by weight, from about 1% to about 12% by weight, or from about 5% to about 9% by weight, based on the total weight of the hair color base and/or hair color composition in which it is present.

The hair color base and/or hair color composition according to the disclosure may comprise at least one fatty substance. "Fatty substance" means an organic compound insoluble in water at normal temperature (25° C.) and at atmospheric pressure (750 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances are, for example, chosen from alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the alkanes, in some embodiments, these have from 6 to 16 carbon atoms and are linear or branched, optionally cyclic. As examples, alkanes can be chosen from hexane and dodecane, isoparaffins such as isohexadecane, isododecane, and isodecane.

Non-limiting examples of non-silicone oils according to the disclosure, include: hydrocarbon oils of animal origin, such as perhydrosqualene; hydrocarbon oils of vegetable origin, such as liquid triglycerides of fatty acids having from 6 to 30 carbon atoms such as oleic acid, triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company F2 Chemicals Ltd.; perfluoro-1,2-dimethylcyclobutane; perfluoroalkanes such as dodecafluoropentane and tetradecafluorohexane, sold under the names "PF 5050e" and "PF 5060e" by the 3M Company, or bromoperfluorooctyl sold under the name "FORALKYL®" by the company Atochem; nonafluoromethoxybutane and nonafluoroethoxyisobutane; derivatives of perfluoromorpholine, such as 4-trifluoromethyl perfluoromorpholine sold under the name "PF 5052e" by the 3M Company.

The fatty alcohols usable as fatty substances according to the disclosure include, but are not limited to, non-alkoxylated, saturated or unsaturated, linear or branched, and have from 6 to 30 carbon atoms and more particularly from 8 to 30 carbon atoms. For example, cetyl alcohol, stearyl alcohol and their mixture (cetearyl alcohol), octyldodecanol, 2-butyloctanol, 2-hexyldecanol, 2-undecylpentadecanol, oleic alcohol or linoleic alcohol may be chosen.

The exemplary non-silicone wax or waxes that can be used in the composition of the disclosure are chosen from paraffin wax, carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; di isopropyl sebacate; diisopropyl adipate; di-n-propyl adipate; dioctyl adipate; di isostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanoate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof. These esters can be for example oleate, laurate, palmitate, myristate, behenate, cocoate, stearate, linoleate, linolenate, caprate, arachidonates, or mixtures thereof such as the oleopalmitate, oleo-stearate, palmitostearate mixed esters.

For example, the mono- and di-esters can be used, and such as the mono- or di-oleate, stearate, behenate, oleopalmitate, linoleate, linolenate, oleostearate, of sucrose, of glucose or of methylglucose. Non-limiting mention can be made of the product sold under the name GLUCATE® DO by the company Amerchol, which is a dioleate of methylglucose.

Exemplary esters or of mixtures of esters of sugar of fatty acid include: the products sold under the names Crodesta™ F160, F140, F110, F90, F70, SL40 by the company Croda, Inc., Edison, N.J., denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Evonik under the name TEGO-SOFT® PSE.

The silicones usable in the composition of the present disclosure include but are not limited to volatile or non-volatile, cyclic, linear or branched silicones, modified or not with organic groups.

The silicones usable according to the disclosure can be in the form of oils, waxes, resins or gums. In some embodiments, a mixture C30-45 alkyldimethylsilyl polypropylsilsesquioxane, available as SW-8005 C30 resin wax available from DOW CORNING®, and paraffin and may be included in the hair color base.

In some embodiments, the silicone is chosen from the polydialkylsiloxanes, such as the polydimethylsiloxanes (PDMS), and the organomodified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C., and for further examples, chosen from: cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula I:

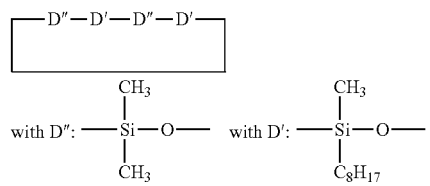

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other suitable volatile silicones include the linear volatile polydialkylsiloxanes having 2 to 9 silicon atoms and with a viscosity less than or equal to $5\times10^{-6}$ m$^2$/s at 25° C. An example is decamethyltetrasiloxane, marketed under the name "Toray SH 200 Fluid" by the company DOW CORNING®. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company Evonik, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of 5×10$^{-6}$ m$^2$/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$, in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from 1×10$^{-5}$ to 5×10$^2$ m$^2$/s at 25° C.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company Genesee Polymers, or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company Evonik.

For example, the fatty substance is chosen from compounds that are liquid or pasty at room temperature and at atmospheric pressure. For further example, the fatty substance is a compound that is liquid at a temperature of 25° C. and at atmospheric pressure.

The fatty substance is, for example, chosen from alkanes, fatty alcohols, esters of fatty acid, esters of fatty alcohol, hydrocarbons, silicones, non-silicone oils, and non-silicone waxes. The non-silicone oils may be selected from mineral, vegetable and synthetic oils.

According to at least one embodiment, the fatty substance is chosen from liquid paraffin, polydecenes, liquid esters of fatty acids and of fatty alcohols, and mixtures thereof. In some embodiments, the fatty substance is chosen from alkanes, hydrocarbons and silicones.

The liquid fatty substances are advantageously chosen from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof. In various embodiments, the liquid fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof.

One liquid fatty substance for use according to the present disclosure is mineral oil which may be commercially available from the supplier Sonneborn under the tradename Kaydol® Heavy White Mineral Oil or from the supplier Exxonmobil Chemical under the tradename Primol™ 352 or from Sonneborn under the tradename Blandol, or from Armedsa under the tradename Aemoil M-302CG or from Exxonmobil Chemical under the tradename Marcol 82.

According to some embodiments, a hair color base may include mineral oil and cetearyl alcohol as fatty substances. For example, the hair color base may include from about 3 to about 7 wt % mineral oil, such as about 4 to about 6 wt %, or about 5 wt %. The hair color base may include from about 3 to about 7 wt % cetearyl alcohol, such as about 4 to about 6 wt %, or about 5 wt %. In some embodiments, the hair color base may include approximately equal amounts of mineral oil and cetearyl alcohol.

In certain embodiments, the at least one fatty substance has a viscosity of about 50 mm$^2$/s or less at 40° C. (kinematic viscosity as measured by the ASTM D 445 method in units of mm$^2$/s at 40° C.). In other embodiments, the at least one fatty substance has a viscosity of greater than about 50 mm2/s at 40° C. and may be chosen from oils such as mineral oil (kinematic viscosity as measured by the ASTM D 445 method in units of mm2/s at 40° C.).

The hair color base and/or hair color compositions may include at least one rheology modifier, for example an acrylic polymer. When present, the at least one acrylic polymer of the present disclosure may, for example, be selected from crosslinked copolymers of (meth)acrylic acid and/or (C1-C6)alkyl esters and from acrylic associative polymers.

The expression "acrylic polymer" is understood, for the purposes of the present disclosure, to mean a polymer that results from the polymerization of one or more monomers.

The acrylic polymer of the present disclosure may also belong to a group of compounds known as acrylic thickening polymers.

The expression "thickening polymer" is understood, for the purposes of the present disclosure, to mean a polymer having, in solution or in dispersion containing 1 percent by weight of active material in water or in ethanol at 25° C., a viscosity greater than 0.2 poise at a shear rate of 1 s−1. The viscosity can be measured with a HAAKE RS600 viscometer from THERMO ELECTRON. This viscometer is a controlled-stress viscometer with cone-plate geometry (for example having a diameter of 60 mm).

As used herein, the term "(meth)acrylic" acid and "(meth) acrylate" are meant to include the corresponding methyl derivatives of acrylic acid and the corresponding alkyl acrylate. For example, "(meth)acrylic)" acid refers to acrylic acid and/or methacrylic acid, and "(meth)acrylate" refers to alkyl acrylate and/or alkyl methacrylate.

In certain embodiments, the acrylic polymer of the present disclosure is selected from crosslinked copolymers of methacrylic acid and of a C1-C6 alkyl ester wherein the C1-C6 alkyl ester is a C1-C6 alkyl acrylate.

Methacrylic acid may be present in amounts ranging from 20 percent to 80 percent by weight, more particularly from 25 percent to 70 percent by weight, such as from 35 percent to 65 percent by weight, relative to the total weight of the copolymer.

The alkyl acrylate may be present in amounts ranging from 15 percent to 80 percent by weight, such as from 25 percent to 75 percent by weight or from 35 percent to 65 percent by weight relative to the total weight of the copolymer. It may be chosen especially from methyl acrylate, ethyl acrylate and butyl acrylate and more particularly ethyl acrylate.

This copolymer may be partially or totally/substantially crosslinked with at least one standard polyethylenically unsaturated crosslinking agent, for instance polyalkenyl ethers of sucrose or of polyols, diallyl phthalates, divinylbenzene, allyl (meth)acrylate, ethylene glycol di(meth)acrylate, methylenebisacrylamide, trimethylolpropane tri(meth) acrylate, diallyl itaconate, diallyl fumarate, diallyl maleate, zinc (meth)acrylate, and castor oil or polyol derivatives manufactured from unsaturated carboxylic acids. The content of crosslinking agent generally ranges from 0.01 percent to 5 percent by weight, such as from 0.03 percent to 3 percent by weight or from 0.05 percent to 1 percent by weight, relative to the total weight of the copolymer.

In certain embodiments, the crosslinked copolymer of methacrylic acid and of a C1-C6 alkyl acrylate is slightly cross-linked. As used herein, the term "slightly crosslinked" refers to a partially crosslinked three-dimensional polymeric network.

In other certain embodiments, the crosslinked copolymer of methacrylic acid and of a C1-C6 alkyl acrylate is alkaliswellable. As used herein, the term "alkali-swellable" as it pertains to the acrylic polymer of the present disclosure refers to a polymer that when introduced to a solution, imparts little or no viscosity, but upon adjusting the pH to mildly acidic, neutral, or mildly basic conditions, a measurable increase in viscosity is observed, i.e., adding an alkali or neutralizing agent to a solution containing an alkali swellable polymer results in the development of viscosity.

The term "alkali-swellable" as used herein may also refer to the expansion of the polymer molecules upon neutralization as a result of charge repulsion of the anionic carboxylate groups of the polymer.

According to one form, the crosslinked copolymer of the invention may especially be in the form of a dispersion of particles in water.

One acrylic polymer of the present disclosure may be chosen from a crosslinked (meth)acrylic acid/ethyl acrylate copolymer, a cross-linked anionic acrylate polymer, and mixtures thereof.

According to one form, the acrylic polymer of the present disclosure selected from a crosslinked (meth)acrylic acid/ ethyl acrylate copolymer and a cross-linked anionic acrylate polymer copolymer may especially be in the form of a dispersion in water. The mean size of the copolymer particles in the dispersion generally ranges from 10 to 500 nm, such as from 20 to 200 nm or from 50 to 150 nm.

In certain embodiments, the crosslinked (meth)acrylic acid/ethyl acrylate copolymer is a crosslinked methacrylic acid/ethyl acrylate copolymer, also known as an acrylates copolymer in aqueous dispersion, an example of which is a slightly cross-linked, alkali-swellable acrylate polymer known by the INCI name acrylates copolymer and commercially available from the supplier Lubrizol, under the trade name Carbopol® Aqua SF-1 as an aqueous dispersion comprising about 30% by weight of total solids or active material. Carbopol® Aqua SF-1 has a carboxyl functionality in its protonated form. This copolymer belongs to a class of synthetic rheology modifiers that include carboxyl functional alkali-swellable and alkali-soluble thickeners (ASTs). These thickener polymers are prepared from the free-radical polymerization of acrylic acid alone or in combination with other ethylenically unsaturated monomers. The polymers can be synthesized by solvent/precipitation as well as emulsion polymerization techniques.

Other suitable crosslinked (meth)acrylic acid/ethyl acrylate copolymers may be chosen from a crosslinked copolymer of methacrylic acid and of ethyl acrylate as an aqueous dispersion containing 38 percent active material, commercially available from the company Coatex under the name Viscoatex™ 538C or a crosslinked copolymer of acrylic acid and of ethyl acrylate as an aqueous dispersion containing 28 percent active material, commercially available from the company Rohm and Haas and sold under the name Aculyn™ 33.

In other certain embodiments, the acrylic polymer of the present disclosure is a cross-linked anionic acrylate polymer. The cross-linked anionic acrylate polymer may be contained in an aqueous dispersion comprising about 32% by weight of total solids. Examples of the cross-linked anionic acrylate polymer of the present disclosure include, but are not limited to, the polymer known by the INCI name acrylates crosspolymer-4 and commercially available from the supplier Lubrizol, under the tradename Carbopol® Aqua SF-2, as an aqueous dispersion comprising about 32% by weight of total solids or active material. Acrylates Crosspolymer-4 may also be described as a copolymer of acrylic acid, methacrylic acid or one of its simple esters, crosslinked with trimethylolpropane triacrylate.

In certain other embodiments, the acrylic polymer of the present disclosure is selected from acrylic associative polymers, also known as acryic associative thickeners. The expression "associative thickener" is understood according to the invention to mean an amphiphilic thickener comprising both hydrophilic units and hydrophobic units, in particular comprising at least one C8-C30 fatty chain and at least one hydrophilic unit.

Acrylic associative thickeners that may be used according to the invention are acrylic associative polymers selected from: (i) nonionic amphiphilic polymers comprising at least one fatty chain and at least one hydrophilic unit; (ii) anionic amphiphilic polymers comprising at least one hydrophilic unit and at least one fatty-chain unit; (iii) cationic amphiphilic polymers comprising at least one hydrophilic unit and at least one fatty-chain unit; (iv) amphoteric amphiphilic polymers comprising at least one hydrophilic unit and at least one fatty-chain unit; the fatty chains containing from 10 to 30 carbon atoms.

Acrylic associative polymers may be chosen from acrylic anionic amphiphilic polymers such as those comprising at least one hydrophilic unit of unsaturated olefinic carboxylic acid type, and at least one hydrophobic unit of (C10-C30) alkyl ester of an unsaturated carboxylic acid type. They may be chosen from those in which the hydrophilic unit of unsaturated olefinic carboxylic acid type corresponds to the monomer of formula (II) below:

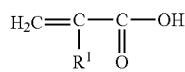

(II)

in which formula R1 denotes H or CH3 or C2H5, i.e. acrylic acid, methacrylic acid or ethacrylic acid units, and the hydrophobic unit of which, of (C10-C30)alkyl ester of an unsaturated carboxylic acid type, corresponds to the monomer of formula (III) below:

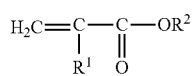

(III)

in which formula R1 denotes H or CH3 or C2H5 (i.e. acrylate, methacrylate or ethacrylate units) and preferably H (acrylate units) or CH3 (methacrylate units), R2 denoting a C10-C30 and preferably C12-C22 alkyl radical.

(C10-C30) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to the U.S. Pat. No. 3,915,921 and U.S. Pat. No. 4,509,949.

The anionic amphiphilic polymers that can be used in the context of the present disclosure may more particularly denote polymers formed from a mixture of monomers comprising:

(i) acrylic acid and one or more esters of formula (IV) below:

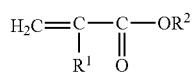

(IV)

in which R1 denotes H or CH3, R2 denoting an alkyl radical having from 12 to 22 carbon atoms, and a crosslinking agent, such as, for example, those constituted of from 95 percent to 60 percent by weight of acrylic acid (hydrophilic unit), 4 percent to 40 percent by weight of C10-C30 alkyl acrylate (hydrophobic unit), and 0 to 6 percent by weight of crosslinking polymerizable monomer, or 98 percent to 96 percent by weight of acrylic acid (hydrophilic unit), 1 percent to 4 percent by weight of C10-C30 alkyl acrylate (hydrophobic unit) and 0.1 percent to 0.6 percent by weight of crosslinking polymerizable monomer; and (ii) essentially acrylic acid and lauryl methacrylate, such as the product formed from 66 percent by weight of acrylic acid and 34 percent by weight of lauryl methacrylate.

The crosslinking agent is a monomer containing a

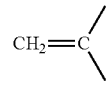

group with at least one other polymerizable group whose unsaturated bonds are not conjugated relative to one another. Mention may be made in particular of polyallyl ethers such as, in particular, polyallyl sucrose and polyallyl pentaerythritol.

Among said polymers above, the products sold by the company Goodrich under the trade names Pemulen™ TR1, Pemulen™ TR2, Carbopol® 1382, and the product sold by the company Coatex under the name Coatex SX®, may be chosen.

Thus, in some embodiments, the acrylic polymer of the present disclosure is selected from an acrylate polymer contained in an aqueous dispersion comprising about 30% by weight of active material. This acrylate polymer may be slightly cross-linked and alkali-swellable.

In other embodiments, the acrylic polymer of the present disclosure is selected from a cross-linked anionic acrylate polymer contained in an aqueous dispersion comprising about 32% by weight of active material.

In yet other embodiments, the acrylic polymer of the present disclosure is chosen from a slightly cross-linked, alkali-swellable acrylate polymer contained in an aqueous dispersion comprising about 30% by weight of active material, a cross-linked anionic acrylate polymer contained in an aqueous dispersion from comprising about 32% by weight of active material, and mixtures thereof.

In some other embodiments, the acrylic polymer of the present disclosure is chosen from acrylic associative polymers, in particular, acrylic anionic amphiphilic polymers which can be selected from those comprising at least one hydrophilic unit of unsaturated olefinic carboxylic acid type, and at least one hydrophobic unit of (C10-C30) alkyl ester of an unsaturated carboxylic acid type.

In certain embodiments, the at least one acrylic polymer of the present disclosure may be a carbomer (4% solution) employed in an amount of from about 0.2% to about 1% by weight, such as from about 0.3% to about 0.0% by weight, from about 0.4% to about 0.8% by weight, or from about 0.5% to about 0.7%, such as at about 0.6% by weight, based on the total weight of the hair color base and/or hair color composition in which it is present.

Thickening agents and rheology modifying polymers other than the above-described acrylic polymers may be added, for example polymeric thickeners and/or non-polymeric thickeners. The polymeric thickener can be chosen from ionic or non-ionic, associative or non-associative polymers. Exemplary polymeric thickeners include various native gums. Representative non-polymeric thickening agents include oxyethylenated molecules and especially ethoxylated alkyl or acyl derivatives of polyols. These polymers can be modified physically or chemically.

When present, the at least one thickening agent may be employed in the compositions of the present disclosure in an amount of from greater than 0% to about 15% by weight, such as from about 0.1% to about 10% by weight, or from about 1% to about 5% by weight, based on the total weight of the hair color base and/or hair color composition in which it is present.

The compositions according to the present disclosure can also comprise at least one cationic polymer. The cationic polymer may be chosen from cationic associative polymers comprising, in their structure, a pendent or terminal hydrophobic chain, for example of alkyl or alkenyl type, containing from 10 to 30 carbon atoms.

The at least one cationic polymer of the compositions can also be chosen from the following:

(1) homopolymers and copolymers derived from acrylic or methacrylic esters or amides, examples of which are: copolymers of acrylamide and of dimethylaminoethyl acrylate quaternized with dimethyl sulfate or with a dimethyl halide, such as the product sold under the name HERCOFLOC by the company Hercules; the copolymers of acrylamide and of methacryloyloxyethyltrimethylammonium chloride described, for example, in EP 80 976 and sold under the name BINA QUAT P 100 by the company Ciba Geigy; the copolymer of acrylamide and of methacryloyloxyethyltrimethylammonium methosulfate sold under the name RETEN by the company Hercules; quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinylpyrrolidone terpolymers, such as the product sold under the name GAFFIX VC 713 by the company ISP; vinylpyrrolidone/methacrylamidopropyldimethylamine copolymers sold, for example, under the name STYLEZE CC 10 by ISP; quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$)alkyltri($C_1$-$C_4$)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide.

In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) Copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) Non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) Polymers of piperazinyl units and of divalent alkylene or hydroxyalkylene radicals.

(5) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) The polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) Cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) Quaternary diammonium polymers.

(9) Polyquaternary ammonium polymers; examples that may be mentioned include the products MIRAPOL A 15, MIRAPOL AD1, MIRAPOL AZ1 and MIRAPOL 175 sold by the company Miranol.

(10) Quaternary polymers of vinylpyrrolidone and of vinylimidazole, for instance the products sold under the names LUVIQUAT FC 905, FC 550 and FC 370 by the company BASF.

(11) Vinylamide homopolymers or copolymers, such as partially hydrolysed vinylamide homopolymers such as poly(vinylamine/vinylamide)s.

(12) Cationic polyurethane derivatives, for example those of elastic nature formed from the reaction: (a1) of at least one cationic unit resulting from at least one tertiary or quaternary amine bearing at least two reactive functions containing labile hydrogen; (a2) of at least one mixture of at least two different nonionic units bearing at least two reactive functions containing labile hydrogen, for instance chosen from hydroxyl groups, primary or secondary amine groups, and thiol groups; and (b) of at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present disclosure include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Useful cationic polymers include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

When present, the cationic polymer may be present in an amount of from greater than 0% to about 5%, such as from about 0.25 to about 3% by weight, or from about 0.5 to about 1.5% by weight, based on the hair color base and/or hair color composition in which it is present.

pH

In some embodiments, the pH of the hair color base and/or the hair color composition may range from about 8.5 to about 10, or such as from about 8.5 to about 9.5, about 9.0 to about 9.5, or about 9.2 to about 9.5. When a colorant is present, the pH of the hair color base and/or hair color composition may vary within the above range according to the type of colorant included therein. If the pH is below about 8.5, the hair color composition may produce an insufficient amount of lift or alteration of color. If the pH is above about 10, the hair color composition may unnecessarily damage hair.

The pH of the oxidizing composition can range from about 2 to about 12, such as from about 6 to about 11, and it may be adjusted to the desired value using acidifying/alkalizing agents that are well known in the art. In certain embodiments, the pH of the oxidizing composition is above 7. In other embodiments the pH of the oxidizing composition may be below 7, such as from about 2 to about 6, or from about 3 to about 5.

The pH of the hair color composition comprising the hair color base composition and the oxidizing component may, in at least certain embodiments, be the same or substantially the same as the pH of the hair color base, for example prior to mixing the hair color base and oxidizing component.

All numbers expressing pH values are to be understood as being modified in all instances by the term "about" which encompasses up to +3%.

Kit and Process of Lifting or Altering the Color of Hair

A further embodiment of the disclosure includes a hair dye "kit" or multi-compartment device in which a first compartment contains a hair color base comprising a buffer system, and optionally a colorant compound, and a second compartment contains one or more oxidizing components. In another embodiment, a hair dye "kit" or multi-compartment device comprises a first compartment containing a hair color base comprising a buffer system, a second compartment containing one or more oxidizing components, and a third compartment containing a colorant or composition comprising a colorant.

As described above, the hair color base may be mixed with an oxidizing component, e.g. at the time of or immediately before it is to be applied to the keratin fibers, such as up to about 30 minutes before, up to about 20 minutes before, or up to about 10 minutes before. The term "mixed" and all variations of this term as used herein refers to contacting or combining or reconstituting or dissolving or dispersing or blending or shaking the hair color base with the oxidizing component. It can also mean introducing the hair color base to the oxidizing component or vice versa. It may also mean placing the hair color base in the same vessel or container as the oxidizing component. A colorant compound may optionally be present in the hair color base and/or the oxidizing component.

The hair color base can be mixed or combined with the oxidizing component in a ratio by weight of from about 1:1 to about 1:10, such as from about 1:1 to about 1:4, such as from about 1:1 to about 1:3, or from about 1:1 to about 1:2.

Thus, a process of lifting or altering the color of hair in accordance with the disclosure comprises contacting a hair color composition comprising the hair color base, an oxidizing component, and optionally a colorant, with the hair. The composition that is applied to hair is formed by mixing the hair color base with the oxidizing component.

In at least certain embodiments, the hair color base and/or hair color composition may exhibit low odor, and/or may not have an unpleasant sensation on the scalp, and thus be more pleasant for the consumer. Additionally, the hair color base and/or hair color composition may be easy to apply, for example with a standard bowl and brush or bottle.

Upon application of the composition comprising the hair color base and the oxidizing component and after an optional resting time (leave-on time) on the hair, for example, ranging from about 1 to about 60 minutes, such as from about 5 to about 45 minutes, from about 5 to about 20 minutes, from about 10 to about 20 minutes, or about 20 minutes, the hair is rinsed, optionally washed with shampoo, rinsed again, optionally washed with a hair conditioning composition, and rinsed again, then dried. The shampoo and hair conditioning composition can be any conventional hair shampoo and conditioner products.

In addition, independently of the embodiment use, the mixture or composition present on the fibers or hair (resulting from the extemporaneous mixing of the compositions, or from the successive application of the hair color base and oxidizing compositions) is left in place for a time, generally, from about 1 to about 60 minutes, such as from about 5 to about 45 minutes, or such as from about 5 to about 20 minutes, or such as from about 10 to about 20 minutes, or such as of about 20 minutes.

The temperature that the process of lifting or altering the color of hair is carried out at is generally between room temperature and 80° C., for example between room temperature and 60° C.

It has been surprisingly discovered that the application of the hair color base and/or hair color composition onto the fibers results in satisfactory lifting or lightening of the color of the fibers, while minimizing damage to the hair fibers compared to commercial or conventional hair color compositions. The coloring obtained using the compositions and process of the present disclosure may also be durable or wash/fade resistant.

The lifting of the color of the hair is evaluated by the tone height or level which describes the degree or level of lift or lightening. The tone heights range from 1 (black) to 10 (light blond), one unit corresponding to one tone; the higher the number, the lighter the shade or the greater the degree of lift.

It was surprisingly and unexpectedly discovered that by using the compositions and process of the present disclosure on hair, the color of the hair was sufficiently lightened such that the degree of lift (increase in tone height) ranged from 0.5 to 4.5, such as up to 2, from 1 to 4, from 1.5 to 2.5, from 2 to 2.5, or about 2. For example, when the starting tone height before treating the hair is 5, and the tone height after treating the hair is 7.5, then the degree of lift or increase in tone height is 2.5. At the same time, the hair treated with the hair color bases and compositions did not feel as rough and did not visually appear to be as damaged as hair treated with conventional dyeing or lifting compositions, indicating less damage to the hair fiber compared to conventional hair coloring compositions, e.g. not comprising the hair color base with the buffer system according to the disclosure.

According to various embodiments, the process and compositions may be used on hair that has not been artificially dyed or pigmented. In further embodiments, the process and composition disclosed herein may be also used on hair that has been artificially dyed or pigmented.

Other than in the operating examples, or where otherwise indicated, all numbers expressing quantities of ingredients and/or reaction conditions are to be understood as being modified in all instances by the term "about" which encompasses ±10%, ±9%, ±8%, ±7%, ±6%, ±5%, ±4%, ±3%, ±2%, or ±1%.

"At least one" as used herein means one or more and thus includes individual components as well as mixtures/combinations.

"Keratin fiber" may be chosen from, for example, human hair.

The term "altering the color" or "color-altering" as used herein may refer lifting or lightening the color of hair. It can also refer to dyeing or coloring hair or depositing color onto the hair. In certain instances, it refers to lifting or lightening the color of hair and depositing color onto the hair at the same time.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

Examples

The amounts of each component in the compositions described below are expressed in % by weight, based on the total weight of the hair color base composition.

TABLE 1

| Hair Color Base Example 1 | |
|---|---|
| INCI US/ingredient | % by weight |
| C30-45 ALKYLDIMETHYLSILYL POLYPROPYLSILSESQUIOXANE (and) PARAFFIN | 2.000 |
| CETEARYL ALCOHOL | 4.000 |
| STEARETH-2 | 2.000 |
| OLEIC ACID | 2.000 |
| LAURYL ALCOHOL | 1.200 |
| MINERAL OIL | 5.000 |
| TWEEN-21 | 3.000 |
| FRAGRANCE | 0.500 |
| CARBOMER (4% SOLUTION IN WATER) | 0.600 |

TABLE 1-continued

Hair Color Base Example 1

| INCI US/ingredient | % by weight |
|---|---|
| AMMONIUM CHLORIDE | 7.000 |
| SODIUM METASILICATE | 3.000 |
| AMMONIUM HYDROXIDE | 3.000 |
| MONOETHANOLAMINE | 3.500 |
| STEARTH-20 | 2.000 |
| POLYQUATERNIUM-6 | 0.920 |
| HEXADIMITHRINE CHLORIDE | 0.360 |
| SODIUM LAURAL SULFATE | 0.550 |
| SODIUM COCOAMPHOACETATE | 2.000 |
| GLYCERIN | 5.000 |

TABLE 1-continued

Hair Color Base Example 1

| INCI US/ingredient | % by weight |
|---|---|
| EDTA | 0.200 |
| SODIUM METABISULFITE | 0.500 |
| ERYTHORBIC ACID | 0.300 |
| DIONIZED WATER | QS 100 |

The hair color base of Example 1 was prepared as follows. Cetearyl alcohol, stereth-2, oleic acid, lauryl alcohol, C30-45 alkyldimethylsilyl polypropylsilsequioxane (and paraffin), and mineral oil were mixed to produce a first mixture. The first mixture was heated at a temperature ranging from about 60° C. to about 80° C. during mixing.

Water and Steareth-20 were mixed to form a second mixture. The second mixture was heated at a temperature ranging from about 60° C. to about 80° C. during mixing.

The first and second mixtures were mixed at low speed in a homogenizer. The speed of the homogenizer was increased to between about 800 and about 1000 rpm and then maintained for about 5 minutes, resulting in a white cream emulsion.

The homogenizer blade was replaced with a chopper blade. Carbomer (4% solution) was added to the emulsion and mixed for about 5 minutes. Glycerine was then added to the emulsion, which was then mixed for about 5 minutes. Sodium lauryl sulfate and sodium metasilicate were added to the emulsion, which was then mixed for about 5 minutes.

Sodium cocoamphoacetate and Tween-21 were then added to the emulsion, which was then mixed for about 10 minutes. Polyquaternium-6 and hexadimethrine chloride were then added to the emulsion, which was then mixed for about 10 minutes. Dyes, sodium metabisulfite, and erythorbic acid were then added to the emulsion, which was then mixed for about 10 minutes.

The emulsion was cooled to about 40° C. Fragrance was then added to the emulsion, followed by about 2 minutes of mixing. Ammonium chloride, monoethanolamine, and ammonium hydroxide were then added to the emulsion, which was then mixed for about 5 minutes. Finally distilled water was added to the emulsion, followed by mixing.

TABLE 2

Hair Color Base Composition Comparative Examples 1, 2, and 3 (conventional/commercial formulas)

| Comparative Hair Color Base Formulas | Key Ingredients |
|---|---|
| Comparative Example 1 (demi-permanent acidic system)* | Ethanolamine (0.2%), nonionic surfactants (17%), cetyl hydroxyethyl cellulose (0.4%), cationic agents (2.5%), glycerin (3%), sodium cetearyl sulfate (1.5%), trideceth-2 carboxaminde MEA (4%), sodium sulfite, erythorbic acid, mica/titanium dioxide, punica gratum seed oil (0.2%), EDTA, water |
| Comparative Example 2 (permanent, alkaline system)* | Ethanolamine (4.2%), nonionic surfactants (33%), carbomer (0.4%), cationic agents (7%), glycol distearate (2%), propylene glycol (10%), lauric acid, silica dimethyl silylate, pentasodium pentetate, sodium metabisulfite, erythorbic acid, mica/titanium dioxide, apricot kernel oil and peach kernel oil (0.2%), water |
| Comparative Example 3 (permanent, alkaline system)* | Ethanolamine (1%), surfactants (24.0%), carbomer (0.4%), cationic agents (2.0%), glycol distearate (2%), propylene glycol (10%), ascorbic acid, cetearyl alcohol, pentasodium pentetate, sodium metabisulfite, erythorbic acid, jojoba seed oil (0.2%), water |

*final composition when the formula is mixed with an oxidizing composition is either alkaline or acidic As shown in Table 2, the comparative hair color base compositions included a demi-permanent acidic system (Comparative Example 1) and two permanent alkaline systems (Comparative Examples 2 and 3). Accordingly, as shown in Tables 3 and 4 below, Example 1 and Comparative Examples 2 and 3 were mixed with an alkaline oxidizing composition, and Comparative Example 1 was mixed with an acidic oxidizing composition.

TABLE 3

Oxidizing Composition (to be mixed with each of Example 1 and Comparative Examples 2 and 3)

| INCI US/Ingredients | Formula I (20 volume)% by weight |
|---|---|
| HYDROGEN PEROXIDE (50% activity in water) | 12 |
| MINERAL OIL | 20 |
| CETEARYL ALCOHOL AND STEARETH-20 | 11 |
| CATIONIC AGENTS - HEXADIMETHRINE CHLORIDE, POLYQUATERNIUM-6 | 0.75 |
| SODIUM STANNATE, PENTASODIUM PENTETATE, TETRASODIUM PYROPHOSPHATE | 0.22 |
| GLYCERIN | 0.5 |
| PHOSPHORIC ACID | pH adjuster |
| WATER | QS 100 |

TABLE 4

Oxidizing Composition (to be mixed with Comparative Example 1)

| INCI US | Formula II (20 volume) % by weight | Formula III (10 volume) % by weight |
|---|---|---|
| HYDROGEN PEROXIDE (50% activity in water) | 12 | 6 |

Other ingredients for each formula: water, glycerin, cetearyl alcohol, ceteareth-25, pentasodium pentetate, tetrasodium pyrophosphate, trideceth-2 carboxaminde MEA, sodium stannate Each of the exemplary and comparative hair color base compositions were mixed with the indicated oxidizing compositions at a 1:1 ratio. However, according to some embodiments, other ratios may be used. For example, a hair color base and oxidizing composition may be mixed in a 1:2 ratio or a 1:3 ratio or a 1:4 ratio.

Table 5 shows pH measurements of the hair color bases of Examples 1 and Comparative Examples 1, 2, and 3, and pH measurement of mixtures including Examples 1 and Comparative Examples 1, 2, and 3 and their corresponding oxidizing compositions. As can be seen in Table 5, the exemplary composition of Example 1 had a pH of 9 before and after mixing with the oxidizing composition. The pH of Comparative Example 1 decreased, due to the addition of the acidic oxidizing compositions. The pH of Comparative Examples 2 and 3 both increased, due to the addition of the alkaline oxidizing composition. As such, Table 5 illustrates that the buffer system of Example 1 was successful in maintaining an alkaline pH that was lower than the pH of the comparable alkaline systems of Comparative Examples 2 and 3.

TABLE 5

Summary of pH

| Mixed Composition | Example 1 | Comp. Example 1 | Comp. Example 2 | Comp. Example 3 |
|---|---|---|---|---|
| pH of Hair Color Base | 9.00 | 7.00-10.20 | 10.15 | 10.38 |
| pH of Mixed Hair Color Base and Oxidizing Composition | 9.00 | 6.50-6.90 | 10.75 | 11.15 |

The above mixtures of compositions were then used on hair according to the following general procedure:
  10 g of the hair color base composition was mixed with 10 g of the oxidizing composition (1:1 ratio);
  the resulting mixture or composition was applied onto hair swatches and left to stand on the hair for about 20 minutes; and
  the hair swatches were then washed with shampoo, rinsed and then dried.

For measuring the degree of change in the color of hair (e.g. degree of lightening/lifting (L) of color or color deposit) after treating the hair, the color of each swatch was measured with a Minolta CM2600d spectrocolorimeter (specular components included, 10 degrees angle, illuminant D65) in the CIEL*a*b* system.

According to this system, the greater the value of L, the lighter or less intense the color. Conversely, the lower the value of L, the darker or more intense the color (this can also indicate greater color deposit when the composition contains colorants).

The following Table 6 shows the color changes imparted to hair samples of the same medium brown color (L value of 22.25), by the exemplary and comparative examples mixed with the corresponding oxidizing compositions, in addition to a control hair sample that was washed but not treated with a composition, after 1 application and after 5 applications.

TABLE 6

L Value results

| Mixture | L value 1X Application | L Value 5X Application |
|---|---|---|
| Control (Wash Only) | 22.25 | 22.25 |
| Example 1 Mixture | 27.98 | 36.42 |
| Comp. Example 1 Mixture | 23.34 | 25.36 |
| Comp. Example 2 Mixture | 26.15 | 34.51 |
| Comp. Example 3 Mixture | 27.59 | 36.47 |

The results of Table 6 show that the Example 1 Mixture produced an amount of lift comparable to that of Comparative Example Mixtures 2 and 3, which were permanent alkaline compositions, as compared to the Control hair. In addition, the Example 1 Mixture also had produced significantly more lift than the demi-permanent acidic composition of the Comparative Example 1 Mixture. However, as shown in Table 5, the Example 1 Mixture had a significantly lower pH than either of the Comparative Example 2 or 3 Mixtures.

The above hair samples were then tested for damage after the first and fifth applications, by detecting amounts of cysteic acid and MEA in each hair sample. The cysteic acid content is one way to measure the amount of damage to hair fibers caused by various chemical treatments performed on hair such as dyeing, lightening and bleaching. The higher the cysteic acid content, and lower amounts of MEA, indicate higher amounts of damage. Table 7 shows the detected amounts of cysteic acid, and Table 8 shows the detected amounts of MEA.

TABLE 7

Cysteic Acid Results (gAA/100gAA)

| Mixture | 1X Application | 5X Application |
|---|---|---|
| Control | 0.70 | 0.70 |
| Example 1 | 0.96 | 1.43 |
| Comp. Example 1 | 0.79 | 1.00 |
| Comp. Example 2 | 1.47 | 2.76 |
| Comp. Example 3 | 1.36 | 2.85 |

TABLE 8

MEA Results (μg/g)

| Mixture | 1X Application | 5X Application |
|---|---|---|
| Control | 179.00 | 179.00 |
| Example 1 | 143.00 | 150.00 |
| Comp. Example 1 | 159.00 | 170.00 |
| Comp. Example 2 | 137.00 | 115.00 |
| Comp. Example 3 | 139.00 | 101.00 |

As can be seen from Tables 7 and 8, the damage produced by the composition of Example 1 was similar to that of the demi-permanent composition of Comparative Example 1. In addition, the damage produced by the Example 1 mixture was significantly less than the damage produced by the permanent alkaline compositions of the Comparative Examples 2 and 3 mixtures. Accordingly, it can be seen that the buffer system of Example 1 produced lift results similar to the Comparative Examples 2 and 3 mixtures, but produced significantly less damage than Comparative Examples 2 and 3 mixtures.

Cosmetic Formulation Examples with Dyes

Colorants 1-12 were each added to the Example 1 Mixture and the Comparative Example 3 Mixture. Table 9 includes the components of Colorants 1-6 and the amounts thereof in wt %, based on the total weight of the corresponding hair color bases. Table 10 includes the components of Colorants 7-12 and the amounts thereof in wt %, based on the total weight of the hair color bases.

TABLE 9

Colorant Compositions 1-6 and Amounts (in wt %)

| Colorant Components | Colorant 1 | Colorant 2 | Colorant 3 | Colorant 4 | Colorant 5 | Colorant 6 |
|---|---|---|---|---|---|---|
| toluene-2,5-diamine | 2.00 | .975 | 1.35 | .600 | | .400 |
| Resorcinol | .910 | .5 | 1.20 | | .462 | .01 |
| p-phenylene-diamine | | | | .345 | | |
| m-Amino-phenol | .200 | .26 | .120 | | .132 | |
| 2,4 Diamino-phenoxy-ethanol HCL | 1.90 | .033 | .100 | | | |
| hydroxy-benzo-morpholine | .150 | | | | | |
| N,N-bis (2-hydroxyethyl)-p-phenylene-diamine sulfate | .230 | | .12 | | | .150 |
| 6-hydroxy-indole | | | | | .0264 | |
| 4-Amino-2-hydroxytoluene | | .065 | | 1.100 | | .510 |
| p-aminophenol | | .325 | | .300 | .275 | |
| 2-methyl-5-hydroxyethyl-aminophenol | | .055 | .500 | | | .150 |
| 2-amino-3-hydroxy-pyridine | | .300 | | | | |
| hydroxypropyl bis (N-hydroxyethyl-p-phenylene-diamine) HCl | | | | | | .200 |
| 4-chloro-resorcinol | | .060 | | | .0264 | |
| hydroxyethoxy aminopyrazolo-pyridine HCl | | | | | .800 | |

TABLE 10

Colorant Compositions 7-12 and Amounts (in wt %)

| Colorant Components | Colorant 7 | Colorant 8 | Colorant 9 | Colorant 10 | Colorant 11 | Colorant 12 |
|---|---|---|---|---|---|---|
| toluene-2,5-diamine | .560 | | .310 | .320 | .060 | .075 |
| Resorcinol | .62 | | .010 | .33 | .150 | .23 |
| m-Amino-phenol | .072 | | | .032 | | .014 |
| 2,4 Diamino-phenoxy-ethanol HCL | .0047 | | | .0012 | | |
| N,N-bis (2-hydroxyethyl)-p-phenylene-diamine sulfate | .046 | | | .05 | | |
| 4-Amino-2-hydroxytoluene | | | .440 | 1.05 | | |
| 2-methyl-resorcinol | | | | | .050 | |
| p-aminophenol | | | .900 | | .150 | .14 |
| 2-methyl-5-hydroxyethyl-aminophenol | | .440 | .500 | | | |
| 1-hydroxyethyl 4,5-diamino pyrazole sulfate | 1.000 | | | | | |
| 2,3-diamino-dihydro-pyrazolo pyrazolone dimetho-sulfonate | .500 | | | | | |
| 4-chloro-resorcinol | | | .074 | .008 | .005 | |

The above colored mixtures were applied to un-permed hair (L value 61.88) and to permed hair samples (L value 60.92). Table 11 below includes the L value results of the colored un-permed hair samples. Table 12 below includes the L value results of the colored permed hair samples.

TABLE 11

Unpermed Hair Sample L Values

| Colorants Included in Mixture | Example 1 Mixture L Values | Comparative Example 3 Mixture L Values |
|---|---|---|
| 1 | 19.65 | 23.1 |
| 2 | 37.47 | 38.29 |
| 3 | 38.6 | 41.6 |
| 4 | 41.64 | 48.67 |
| 5 | 25.33 | 27.74 |
| 6 | 53.10 | 56.6 |
| 7 | 55.10 | 58.1 |
| 8 | 43.10 | 45.3 |
| 9 | 41.60 | 53.1 |
| 10 | 53.34 | 55.36 |
| 11 | 57.78 | 58.2 |
| 12 | 58.30 | 59.6 |

TABLE 12

Permed Hair Sample L Values

| Colorants Included in Mixture | Example 1 Mixture L Values | Comparative Example 3 Mixture L Values |
|---|---|---|
| 1 | 18.37 | 20.9 |
| 2 | 35.97 | 37.27 |
| 3 | 36.48 | 40.1 |
| 4 | 43.21 | 47.49 |
| 5 | 32.17 | 25.69 |
| 6 | 52.14 | 53.14 |
| 7 | 56.14 | 57.35 |
| 8 | 40.17 | 43.12 |

TABLE 12-continued

Permed Hair Sample L Values

| Colorants Included in Mixture | Example 1 Mixture L Values | Comparative Example 3 Mixture L Values |
|---|---|---|
| 9 | 49.15 | 50.12 |
| 10 | 47.25 | 53.69 |
| 11 | 56.25 | 57.15 |
| 12 | 57.83 | 58.78 |

The compositions prepared using the Example 1 mixture imparted excellent color deposit as evidenced by the significantly lower L values compared to the L values for untreated hair (both permed and unpermed). At the same time, using the same dye concentrations, the hair contacted with the compositions prepared using the Example 1 mixture exhibited comparable and/or greater color deposit as evidenced by the L values as compared to the hair contacted with the compositions prepared using the Comparative Example 3 mixture.

The results in the above tables surprisingly and unexpectedly showed that the composition of the invention consistently lifted the color of the hair by two levels, i.e., the degree of lift was 2 or more. This color lifting capability of the inventive composition allows for enhanced gray coverage when dye compounds are present in the inventive hair color composition. Further, the hair color composition provides lift and/or coloration amounts similar to conventional alkaline permanent dye compositions, but with significantly less damage to hair.

It will be apparent to those skilled in the art that various modifications and variations can be made in the delivery system, composition and methods of the invention without departing from the spirit or scope of the invention. Thus, it is intended that the present disclosure cover the modifications and variations of this invention provided that they come within the scope of the appended claims and their equivalents.

What is claimed is:

1. A hair color base comprising an alkalizing buffer system, wherein the buffer system comprises, based on the total weight of the hair color base:
    from about 3 wt % to about 12 wt % of ammonium chloride;
    from about 1 wt % to about 5 wt % of sodium metasilicate;
    from about 1 wt % to about 5 wt % of ammonium hydroxide; and
    from about 1 wt % to about 5 wt % of monoethanolamine (MEA), and wherein the hair color base has a pH ranging from about 8.5 to about 10.

2. The hair color base according to claim 1, having a pH in the range of about 9.0 to about 9.5.

3. The hair color base according to claim 1, wherein the buffer system comprises, based on the total weight of the hair color base, from about 6 wt % to about 8 wt % of ammonium chloride, from about 2 wt % to about 4 wt % of sodium metasilicate, from about 2 wt % to about 4 wt % of ammonium hydroxide, and from about 2.5 wt % to about 4.5 wt % of MEA.

4. The hair color base according to claim 1, wherein the hair color base further comprises at least one colorant compound.

5. The hair color base according to claim 4, wherein the at least one colorant compound is chosen from oxidation dye precursors.

6. A hair color composition comprising:
    a hair color base comprising an alkalizing buffer system, wherein the buffer system comprises, based on the total weight of the hair color base:
        from about 3 wt % to about 12 wt % of ammonium chloride;
        from about 1 wt % to about 5 wt % of sodium metasilicate;
        from about 1 wt % to about 5 wt % of ammonium hydroxide; and
        from about 1 wt % to about 5 wt % of monoethanolamine (MEA);
    at least one oxidizing component, and
    optionally at least one colorant, and
    wherein the hair color base has a pH ranging from about 8.5 to about 10.

7. The hair color composition according to claim 6, having a pH in the range of about 9.0 to about 9.5.

8. The hair color composition according to claim 6, wherein the buffer system comprises, based on the total weight of the hair color base, from about 6 wt % to about 8 wt % of ammonium chloride, from about 2 wt % to about 4 wt % of sodium metasilicate, from about 2 wt % to about 4 wt % of ammonium hydroxide, and from about 2.5 wt % to about 4.5 wt % of MEA.

9. The hair color composition according to claim 6, wherein the hair color base comprises at least one colorant.

10. The hair color composition according to claim 9, wherein the at least one colorant is chosen from oxidation dye precursors.

11. A method for altering the color of hair, comprising contacting hair with a composition for a sufficient period of time to achieve a desired level of lift of the color of the hair, wherein the composition is formed from mixing (a) a hair color base comprising an alkalizing buffer system with (b) an oxidizing component, wherein:
    the buffer system comprises, based on the total weight of the hair color base, from about 3 wt % to about 12 wt % of ammonium chloride, from about 1 wt % to about 5 wt % of sodium metasilicate, from about 1 wt % to about 5 wt % of ammonium hydroxide, and from about 1 wt % to about 5 wt % of monoethanolamine (MEA); and
    the pH of the composition ranges from about 8.5 to about 10.

12. The method according to claim 11, further comprising leaving the composition on the hair for a time period of up to about 60 minutes.

13. The method according to claim 11, wherein the pH of the composition ranges from about 9.0 to about 9.5.

14. A multi-compartment kit for altering the color of the hair, comprising:
    (a) a first compartment comprising a hair color base comprising an alkalizing buffer system, wherein the buffer system comprises, based on the total weight of the hair color base, from about 3 wt % to about 12 wt % of ammonium chloride from about 1 wt % to about 5 wt % of sodium metasilicate, from about 1 wt % to about 5 wt % of ammonium hydroxide, and from about 1 wt % to about 5 wt % of monoethanolamine (MEA), wherein the hair color base has a pH ranging from about 8.5 to about 10; and
    (b) a second compartment comprising an oxidizing composition comprising at least one oxidizing agent.

15. The multi-compartment kit according to claim 14, wherein the buffer system is configured to buffer a mixture of the hair color base and the alkaline oxidizing composition to a pH ranging from about 9.0 to about 9.5.

* * * * *